(12) United States Patent
Ross

(10) Patent No.: US 7,077,289 B2
(45) Date of Patent: Jul. 18, 2006

(54) POWERED DISPENSER FOR INTERCONNECTED STRIP BANDAGES

(76) Inventor: Nadine Ross, 25055 Hwy. 395 North, Kettle Falls, WA (US) 99141

( * ) Notice: Subject to any disclaimer, the term of this patent is extended or adjusted under 35 U.S.C. 154(b) by 464 days.

(21) Appl. No.: 10/444,554

(22) Filed: May 27, 2003

(65) Prior Publication Data

US 2004/0238559 A1 Dec. 2, 2004

(51) Int. Cl.
B65H 5/00 (2006.01)
B65H 5/28 (2006.01)
B65H 11/68 (2006.01)
B65H 18/08 (2006.01)

(52) U.S. Cl. .................. 221/225; 221/72; 242/530; 242/535.3; 242/535.2; 242/538.1; 242/538.2; 242/538.3

(58) Field of Classification Search ........... 221/225, 221/72; 242/530, 535.3, 535.2, 538.1, 538.2, 242/538.3; 156/344, 584, 351, 494, 541
See application file for complete search history.

(56) References Cited

U.S. PATENT DOCUMENTS

| | | | | |
|---|---|---|---|---|
| 3,652,539 A | * | 3/1972 | Miura et al. ............... 536/85 |
| 4,422,376 A | * | 12/1983 | Teraoka .................. 101/69 |
| 4,836,594 A | * | 6/1989 | Spreiter .................. 294/1.3 |
| 4,872,593 A | * | 10/1989 | Behringer ................ 221/231 |
| 5,065,894 A | * | 11/1991 | Garland .................. 221/25 |
| 5,133,821 A | * | 7/1992 | Jensen ................... 156/245 |
| 5,249,705 A | * | 10/1993 | Gates ..................... 221/6 |
| 5,344,043 A | * | 9/1994 | Moulding et al. .......... 221/71 |
| 5,891,078 A | * | 4/1999 | Turngren et al. .......... 602/58 |
| 6,003,722 A | * | 12/1999 | Thurner .................. 221/25 |
| 6,162,159 A | * | 12/2000 | Martini et al. ........... 493/324 |
| 6,299,018 B1 | * | 10/2001 | Kimbrell ................. 221/71 |
| 6,652,173 B1 | * | 11/2003 | Martini et al. ........... 400/621 |
| 6,755,321 B1 | * | 6/2004 | Solovay et al. ........... 221/73 |
| 6,786,360 B1 | * | 9/2004 | Vogt et al. .............. 221/268 |

FOREIGN PATENT DOCUMENTS

| | | |
|---|---|---|
| DE | 3128547 A1 * | 2/1983 |
| EP | 0585145 B1 * | 3/1994 |

* cited by examiner

Primary Examiner—Gene O. Crawford
Assistant Examiner—Michael E. Butler
(74) Attorney, Agent, or Firm—Keith S. Bergman; William A. Jeckle

(57) ABSTRACT

A dispenser for individual strip bandages from a rolled elongate bandage supply having the individual strip bandages releasably interconnected between a pair of cover strips defining chambers about each strip bandage. The dispenser provides a feed spindle carrying the bandage supply that is moved to a cover strip separator adjacent to a delivery slot in a casement. The cover strips are removed from a given strip bandage in the separator and pass along waste courses to motor powered take-up devices which move the bandage supply and disperse the given strip bandage through the delivery slot. At least one cover strip waste course has a tension sensor to sense tension in the associated cover strip to control the take-up device moving the associated cover strip to maintain synchronization of the motion of the pair of cover strips on the take-up devices moving them.

5 Claims, 3 Drawing Sheets

POWERED DISPENSER FOR INTERCONNECTED STRIP BANDAGES

II. BACKGROUND OF INVENTION

II.A Related Applications

There are no applications related hereto heretofore filed in this or any foreign country.

II.B Field of Invention

My invention relates generally to article dispersing and more particularly to a powered dispenser for a rolled elongate strip of adhesive bandages carried between opposed cover strips.

II.C Background and Description of Prior Art

Since the advent of bandages that combined an absorbent material with an adhesive element this type of bandage has become increasing popular and in the present day has become fairly sophisticated and somewhat standardized in configuration. This type of bandage in its earlier developmental stages was individually packaged or containerized in some type of casement that maintained sterility until the time of use as epitomized by the Band-Aid® of Johnson & Johnson Pharmaceutical Company (hereinafter generically "strip bandage") widely used in individual packaging, especially by individuals and non-professional users. Since strip bandages also have become widely used by medical professionals, such as physicians, surgeons, nurses and institutional and laboratory employees, specialized bulk packaging of such bandages has been developed for this use to provide substantial quantities of strip bandages and make their use as convenient and time efficient as possible, in view of the relatively high cost of medical services which seems to rise continuously in the present economy with the passage of time. Responsive to medical professional use various mechanical devices to aid dispersement of strip bandages in an individual fashion and ready for use from their sterile containment have been developed.

Initially such mechanical devices merely removed, or aided the removal, of sanitary cover strips from one of a supply of individual unconnected strip bandages. As time progressed a plurality of strip bandages carried in individual sanitized chambers were interconnected with each other to aid in making the dispersement process more efficient. Generally the supply of strip bandages was enclosed in individual chambers defined between two elongate cover strips provided in either rolled or folded form for simple sequential mechanical dispersement. Such dispersement devices have attained sophistication during their historical period of development, but notwithstanding this sophistication problems still remain with the device, some of which the instant invention seeks to resolve by providing a new powered opening and dispersement mechanism for rolls of sanitarily encased strip bandages.

A problem arises in mechanically dispersing strip bandages from a rolled supply source that can be troublesome, but does not appear to have been addressed by the prior art. When a length of strip bandages carried between two cover strips is rolled, the cover strip on the outer side of the roll of such bandages is necessarily longer than the cover strip on the inner side, as the outer cover strip of each layer passes about a course of greater circumferential length than does the inner cover strip. This difference in length of the cover strips is cumulative throughout the length of the strip bandage supply roll. The problem manifests itself when individual bandages in the supply roll are dispersed in a mechanism that moves the supply roll by moving and simultaneously stripping the cover strips from each side of the strip bandage roll as the cover strip on the inner side of the supply roll will have less length to become more tight and the cover on the outer side of the supply roll will have more length to become more loose. This action, if not accommodated, disrupts synchronization of take up type waste rolls if used as feeding mechanism and can cause malfunction of the feeding structure, disrupt its operability and require substantial maintenance activity.

The instant dispenser resolves this problem by providing sensors to sense tension in both the inner and outer cover strips between the supply roll and the waste rolls upon which the cover strips are wound to move the bandage supply toward the point of dispersement of strip bandages. The motion of each waste roll is determined responsive to the sensed tension in the cover strip wound thereon to maintain constant predetermined tension in both the inner and outer cover strips being rolled on the respective waste rolls. This regulation of tension in the waste rolls that ultimately moves the bandage strip from its supply roll automatically regulates the motions of the waste rolls to accommodate the longer length of the radially outer cover strip and the shorter length of the radially inner cover strip to maintain synchronization of the operation of the dispenser at all times, regardless of the amount of bandage strip on the supply roll or the lengths of cover strips on the waste rolls. This method of measuring tension in the cover strips passing to the waste rolls to regulate motion of the waste rolls not only resolves the problem of waste roll synchronization for both the radially inner and outer cover strips, but also allows the use of relatively simple mechanism to provide a dispenser having faithful, maintenance free operation that can be manufactured at a relatively low, economically reasonable cost to allow use not only by professional users but also by non-professional users.

III. SUMMARY OF INVENTION

My invention generally provides a dispenser for individual strip bandages from a rolled bandage supply having a plurality of strip bandages each carried in sealed sanitary chambers defined between opposed cover strips on each side of the strip bandages. The dispenser provides a peripherally defined casement carrying a feed spindle that supports the rolled bandage supply for motion adjacent to a delivery slot defined in the casement. A separator directs the cover strips in opposite directions from the delivery slot and along separate waste paths to powered take-up reels which move the bandage supply from the supply roll to disperse strip bandages through the delivery slot ready for use. Each cover strip waste course has an associated slack sensor, between the separator and the respective take-up reels, to sense tension in the cover strip waste course and responsively control take-up reel motion to maintain predetermined tension which maintains synchronization of the take-up reels notwithstanding difference in the length of the covering strips being wound thereon.

In creating such a dispenser, it is:

a principal object to provide a powered dispenser for a rolled bandage supply of strip bandages carried in individual sanitary chambers defined between two cover strips on each side of the strip bandages.

A further object is to provide such a dispenser that moves the rolled bandage supply by moving each of the cover strips onto powered take-up reels while dispersing bandages carried between the cover strips for sequential use at a point adjacent that whereat the cover strips are separated from the encased strip bandages.

A still further object is to provide tension sensors in the waste paths of each cover strip, between the separator and each respective take-up reel, to sense tension in each cover strip and responsively determine take-up reel motion to maintain predetermined tension in each cover strip to allow cover strips of unequal length to be synchronously rolled on the associated take-up reel.

A still further object is to provide such a dispenser that may be operated by switch activation to disperse a bandage ready for use.

A still further object is to provide such a dispenser that is of new and novel design, of rugged and durable nature, of simple and economic manufacture and one that is otherwise well suited to the uses and purposes for which it is intended.

Other and further objects of my invention will appear from the following specification and accompanying drawings which form a part hereof. In carrying out the objects of the invention, however, it is to be understood that its essential features are susceptible of change in design and structural arrangement with only one preferred and practical embodiment being illustrated and specified as is required, but such specification is not intended to limit the invention other than as set forth in the appended claims.

IV. BRIEF DESCRIPTION OF DRAWINGS

In the accompanying drawings which form a part hereof and wherein like numbers of reference refer to similar parts:

V. DESCRIPTION OF THE PREFERRED EMBODIMENT

Figure 1:
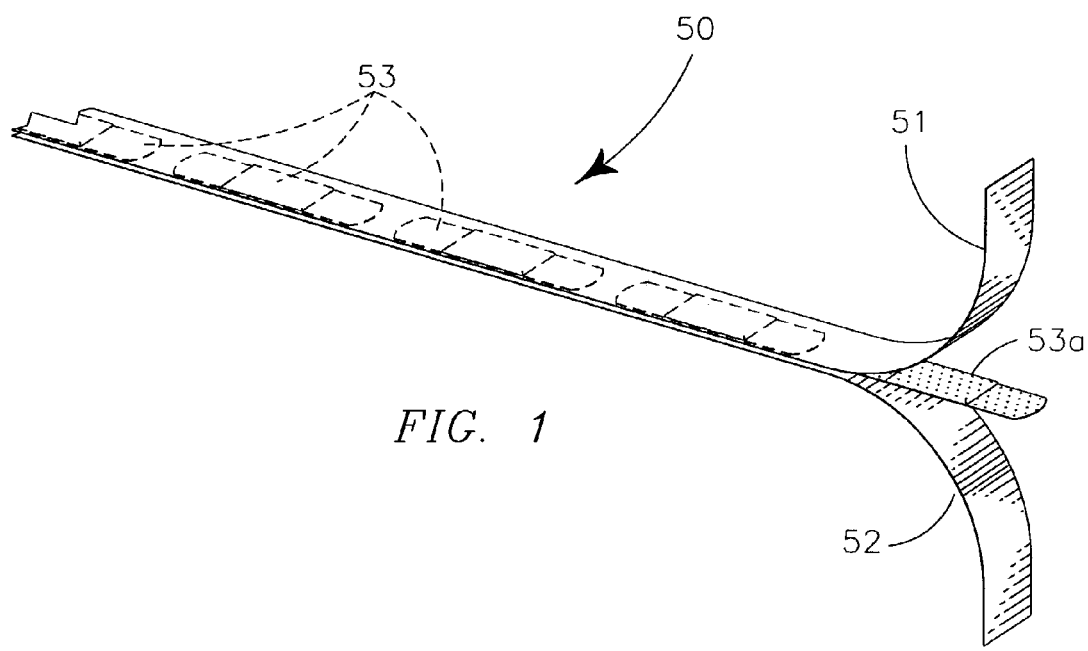
FIG. 1 is an isometric view of a portion of a covered supply of strip bandages that are used with my dispenser, with the covering strips partially removed.

My dispenser apparatus 100 provides casement 110 carrying bandage supply 50 on bandage support device 120 to pass the bandage supply 50 through cover strip separator device 130 to separate cover strips of the bandage supply 50 and pass them along first waste path 21 and second waste path 22 to first cover strip take-up device 140 and second cover strip take-up device 150, respectively. The take-up devices 140,150 are powered by first motor 160 and second motor 170 respectively. Each waste path 21, 22 has associated first tension sensor 180 and second tension sensor 190 respectively to control motion of first motor 160 and second motor 170 respectively.

Figure 3:
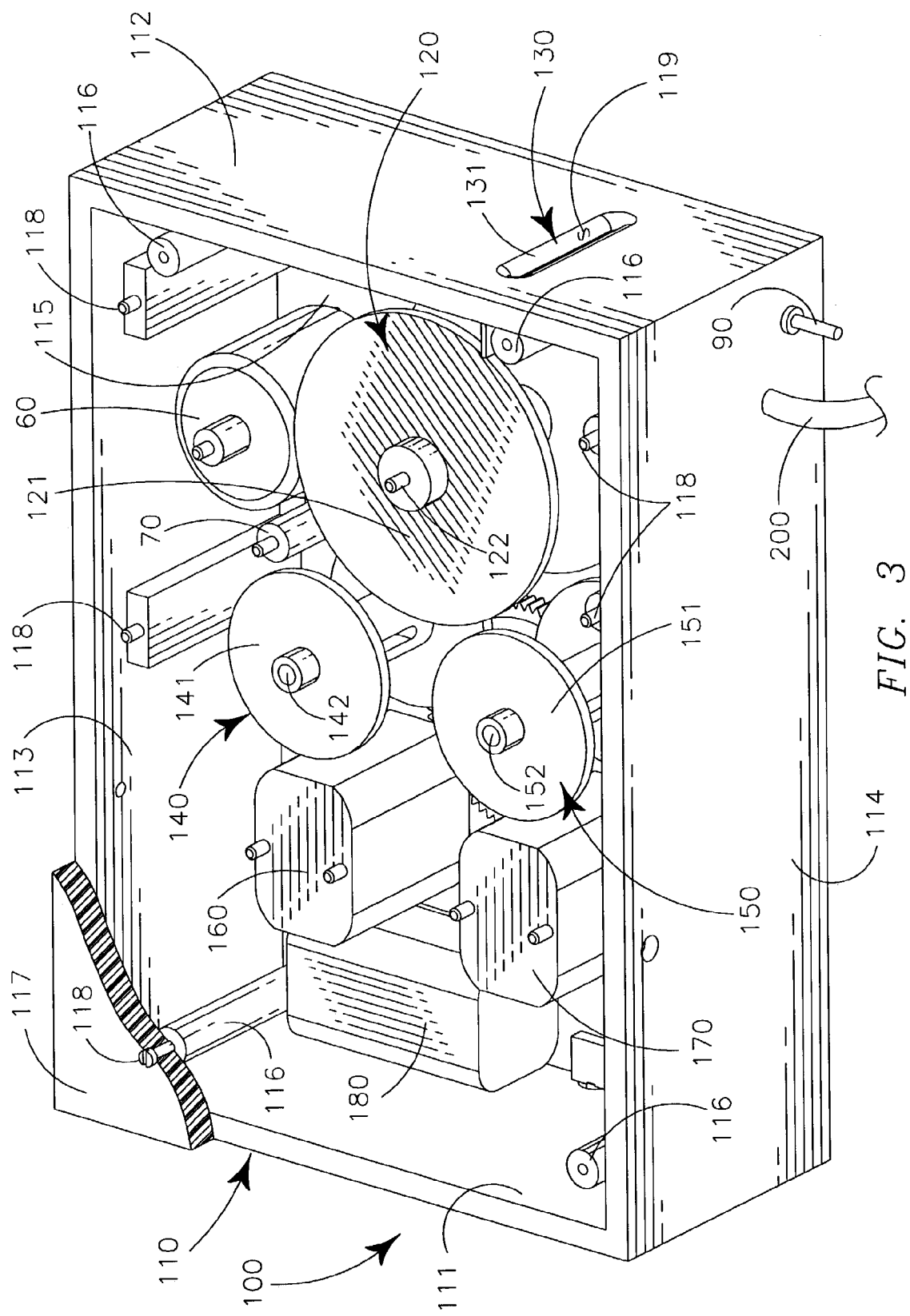
FIG. 3 is a downward and rearward looking isometric view of a dispenser with the top of the casement partially cutaway to show various of its parts, their configuration and relationship from this aspect.

FIG. 3 is an isometric view dispenser apparatus 100 in accordance with one specific embodiment of the invention. The dispenser apparatus 100 is generally configured to disperse bandages (not shown) as described in greater detail hereinafter. The dispenser apparatus 100 includes casement 110, substantially in the form of a box, which is fabricated from durable structural material to provide support and protection for the various components supported therein.

The casement 110 has back 111, bottom 115 and similar sides 113 and 114. The casement 110 furthermore has top panel 117 which has been partially cutaway in FIG. 1 in order to show the internal components of the dispenser apparatus 100. The casement 110 illustrated is substantially rectilinear with the top panel 117 and the bottom 115 spaced apart in substantially parallel juxtaposed relation to one another, with the sides 113 and 114 extending therebetween in substantially parallel juxtaposed relation to one another.

Preferably the top panel 117, bottom 115, sides 113, 114 and back 111 are in the form of substantially flat panels as shown, with each of the panels joined together at adjacent surfaces to form a rigid enclosure. The top panel 117 is removably mounted to the casement 110 opposite the bottom 115 to completely enclose the casement. The top panel 117 may be removably mounted to the casement 110 by various known methods such as in the instance illustrated by way of mounting posts 116 and bolts 118 passing through the top panel 117 and into threaded engagement in the mounting posts 116, which also serve as separators.

A slot 119 is defined in the casement 110 as shown. By way of example only, the slot 119 is defined through front 112 of the casement 110, however, it is to be understood that alternatively, the slot 119 can be defined in other portions of the casement 110. The slot 119 allows strip bandages (not shown in FIG. 3) to pass through the casement 110 during dispersement as explained in greater detail hereinafter. A cover strip separator device 130 is supported on the casement 110 in a position inwardly adjacent to the slot 119 as is shown. The details of the separator device 130 are specified in greater detail hereinafter.

A manually operable switch 90 is supported by the casement 110 as shown with its operative element extending from the external surface of casement 110. The switch 90 can be variously positioned so that an operator of the dispenser apparatus 100 can operate the switch externally of the casement with relative ease. The switch 90 can be of various known forms such as a toggle switch (as is shown), a push-button switch, a pull-cord switch or the like. Furthermore, the switch 90 can incorporate other features and elements that are not specifically described herein, such as by way of example only, various timers, sensors and detection devices that function to control the operation of the dispenser apparatus 100 in the general manner hereinafter described.

Figure 2:
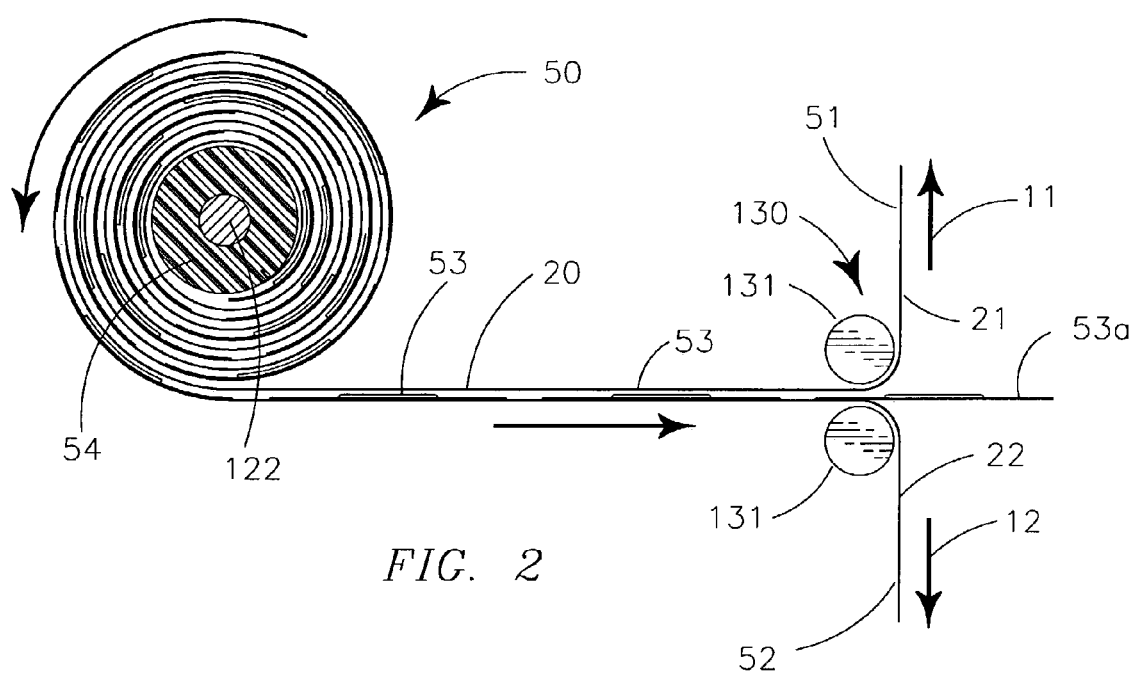
FIG. 2 is a somewhat diagrammatic plan view of a rolled supply of strip bandages passing through a dispenser for delivery of an individual strip bandage for use.

The dispenser apparatus 100 provides bandage support device 120 configured to support a bulk rolled bandage supply 50. The bandage support device 120 is supported on the bottom 115 of casement 110. By way of example only, the bandage support device 120 illustrated is in the form of a reel 121 that is rotatably mounted on axle 122, which is rigidly supported on the bottom 115 of the casement 110. The reel 121 is configured to be removable from the axle 122 to facilitate loading the bulk bandage supply 50 into the dispenser apparatus 100 and provides a predetermined friction between the reel 121 and axle 122 which must be overcome to allow rotation of the reel 121 for movement of the bulk bandage supply 50 therefrom. Various known friction generating devices and processes may be used to create the predetermined friction such as providing a bandage supply reel 121 with an arbor 54 (FIG. 2) with an axial channel that frictionally engages about axle 122.

The dispenser apparatus 100 includes a pair of cover strip take-up devices 140 and 150. Each cover strip take-up device 140, 150, by way of example only, is in the form of a flanged spool or reel 141, 151 that is irrotatably supported on respective axles 142, 152 respectively. Each of the reels 141, 151 are configured to be removable from the respective axle 142, 152 supporting them for removal or wastage of cover strips carried thereon.

The dispenser apparatus 100 includes two motors 160, 170 preferably of an electrically powered type to make regulation of speed more simple and easy. The first motor 160 is supported on casement 110 in power-transmitting engagement with the first cover strip take-up device 140 and the second motor 170 is supported on the casement 110 in power-transmitting engagement with the second cover strip take-up device 150. The dispenser apparatus 100 further includes a power supply 180, such as a battery or other alternating current or direct current source. The power supply 180 is configured to supply operational power to the motors 160, 170 and other electrically powered control and sensing devices.

FIG. 1 shows an isometric view of the bandage supply 50 which is configured to be employed in conjunction with the dispenser apparatus 100. The bandage supply 50 includes a plurality strip of bandages 53 that can be of a type that is known in the art. The bandage supply 50 provides a pair of elongate cover strips 51, 52 that are fabricated from a flexible material such as paper, sheet plastic, cloth or the like. The bandages 53 preferably are arranged in end-to-end orientation between the cover strips 51, 52 as depicted, however, it is to be understood that the bandages 53 can be oriented in other alternative orientations as well.

The first cover strip 51 and the second cover strip 52 preferably are adhered to one another by way of an adhesive (not shown) or are otherwise fastened in a manner such that each of a plurality of bandages 53 is "sandwiched" between the first and the second cover strips 51, 52 in pockets or chambers defined therebetween to maintain a separate sterile environment for each of the plurality of bandages 53. With this structure the first cover strip 51 and the second cover strip 52 can be separated from each other to dispense a given bandage 53a. That is, when the bandage supply 50 is configured in such a manner, the first cover strip 51 and the second cover strip 52 can be pulled apart from each another to expose the given bandage 53a to facilitate the dispersing of the given bandage 53a through slot 119 to a user of the dispenser apparatus 100.

FIG. 1 shows a plan view of the bulk bandage supply 50 along with a schematic depiction of the cover strip separator device 130. The cover strip separator device 130 provides a pair of adjacent cylindrical posts 131, or rollers. As is also shown, the bulk bandage supply 50 which initially is in the form of a coiled roll is threaded between the adjacent cylindrical posts 131 of the cover strip separator device 130.

With the first cover strip 51 and the second cover strip 52 threaded between the posts 131 of the cover strip separator device 130, the first cover strip 51 is pulled in a first direction 11 while the second cover strip 52 is pulled in a second direction 12. In this manner, the first cover strip 51 is separated from the second cover strip 52 to dispersably expose the individual bandage 53a. Furthermore, as the first cover strip 51 and the second cover strip 52 are pulled in the manners described, the coiled roll of the bandage supply 50 that is rotatably supported on axle 122 is responsively uncoiled as successive bandages 53 are dispersed.

Figure 4:
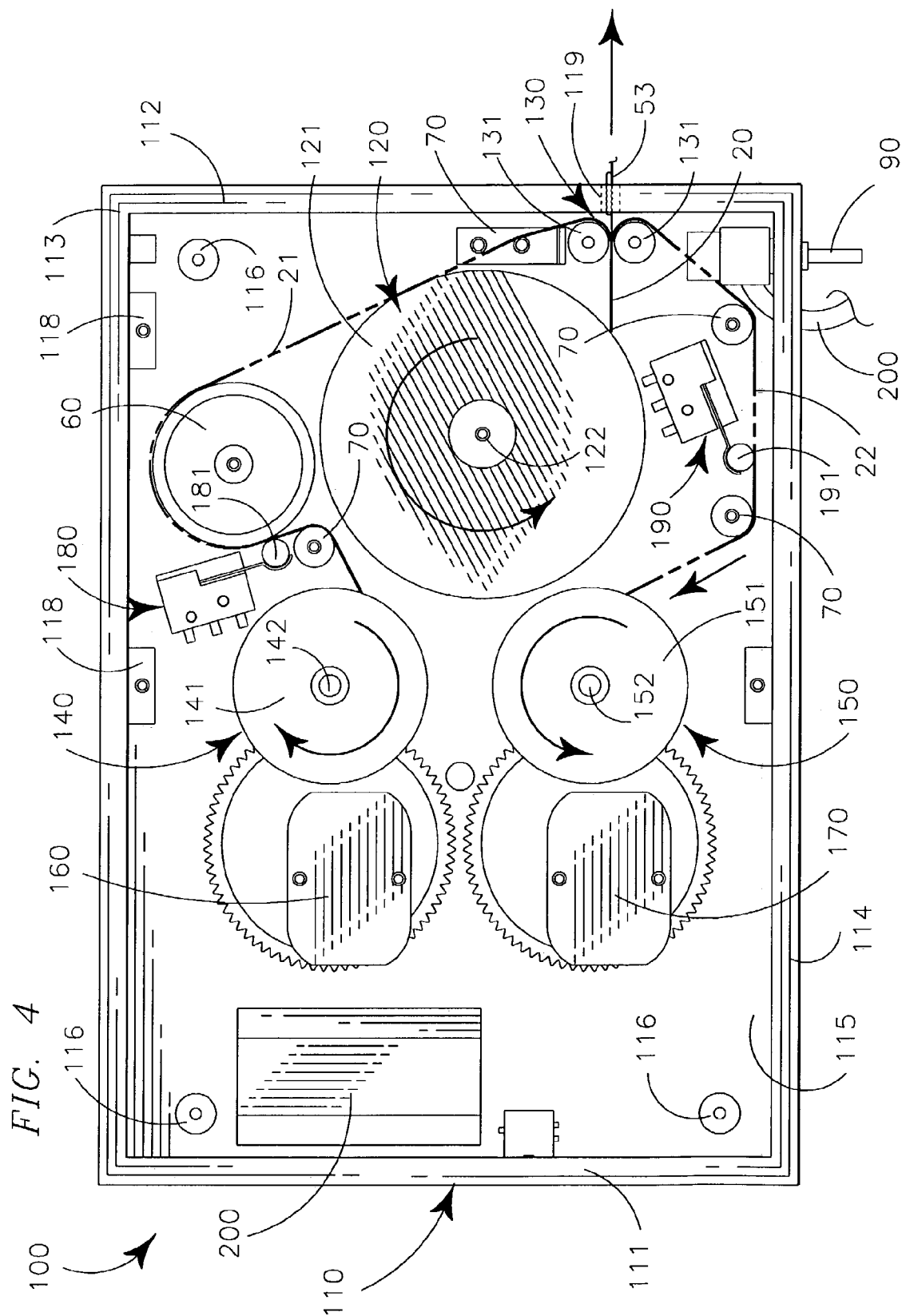
FIG. 4 is plan view of the dispenser of FIG. 3 with the casement top removed to show various dispenser parts from this aspect, and particularly the course of travel of the bandage supply and covering strips through the dispenser.

FIG. 4 shows a plan view in which the dispenser apparatus 100 is depicted with the top panel 117 removed. As is seen, a main bandage path 20 is defined from the bandage support device 120 to the cover strip separator device 130. A first waste path 21 is defined from the cover strip separator device 130 to the first cover strip take-up device 140. A second waste path 22 is defined from the cover strip separator device 130 to the second cover strip take-up device 150.

Various rollers and posts can be included in the dispenser apparatus 100 to serve to partially define portions of one or more of the paths 20, 21, 22. For example, roller 60 can be rotatably supported by the casement 110 to define a portion of the first waste path 21. Various other posts, rollers 70, or the like can be supported on the casement 110 to partially define a portion of one or more of the paths 20, 21, 22, as also is illustrated.

At least one tension sensor 180, 190 is associated with each waste path. In the instance illustrated in FIG. 4 first tension sensor 180 is supported by casement 110 adjacent to first waste path 21 and second tension sensor 190 is supported by the casement 110 adjacent to second waste path 22. Each tension sensor 180, 190 provides a sensing arm 181, 191 respectively that contacts the adjacent cover strip in path 21, 22 respectively to sense the tension in the contacted cover strip. Responsive to the sensed tension each tension sensor 180, 190 regulates the motion of motors 160, 170 respectively to maintain a predetermined tension in the cover strips in the waste paths 21, 22 respectively. To create tension in the cover strips 51, 52, the bandage support device 120 preferably provides a frictionally restrained rotary motion of the arbor 54 of reel 121 on the axle 122 carrying it.

In operation of the dispenser apparatus 100, the top panel 117 is first removed to expose the various internal components of the casement 110 as depicted in FIG. 4. The reel 121 carrying a coiled roll of bandage supply 50 (shown in FIGS. 1 and 2) is placed into the casement 110 on the axle 122 so as to be frictionally rotatable relative to the casement 110.

Once the bulk bandage supply 50 is placed in a supported position in the casement 110, the first and second cover strips 51, 52 are threaded through the cover strip separator device 130 and between cylindrical posts 131. At this point, the first and second cover strips 51, 52 along with the bandages 53 that are carried therebetween are oriented to substantially follow the bandage path 20 from the bandage support device 120 to the strip separator device 130.

The first cover strip 51 (shown in FIGS. 2 and 3) is then threaded along the first waste path 21 and then attached to the first cover strip take-up device 140. Similarly, the second cover strip 52 (also shown in FIGS. 2 and 3) is threaded along the second waste path 22 and then attached to the second cover strip take-up device 150. More specifically the first cover strip take-up device 140 includes the first flanged spool 141 to which the first cover strip 51 is attached for winding thereabout. Similarly, the second cover strip take-up device 150 includes the second flanged spool 151 to which the second cover strip 52 is attached for winding thereabout. At this point, the top panel 117 is placed back onto the casement 110 and fastened thereto to cover the internal components carried in the casement 110 along with the bulk bandage supply 50. The dispenser apparatus 100 now is ready for operation to selectively disperse individual bandages 53 by operation of the apparatus.

When an operator of the dispenser apparatus 100 desires to dispense the bandage 53a therefrom, the operator manipulates the switch 90. The switch 90 is controllably linked with the motors 160, 170 and can be manipulated to cause the motors to operate by drawing power from power supply 200.

In operation the motors 160, 170 engage the respective cover strip take-up devices 140, 150. The switch 90 can be selectively actuated to operate either or both of the motors 160, 170.

In the instance discussed, wherein the cover strip take-up devices 140, 150 include respective flanged spools 141, 151, the respective motors 160, 170 operate to rotate the respective associated flanged spool. By way of example only, the flanged spools 141, 151 can be caused to rotate in the directions indicated. Such rotation of the flanged spools 141, 151 causes the respective first and second cover strips 51, 52 to be wound thereupon. Responsively, the winding of the first and second cover strips 51, 52 about the respective flanged spools 141, 151 causes the cover strips and covered bandages to unroll from the reel 121 which is caused to rotate about the axle 122 in the direction indicated against its frictional bias.

The winding of the first and second cover strips 51, 52 on flanged spools 141, 151 is controlled by first and second tension sensors 180, 190 respectively. The tension sensors 180, 190 sense tension in each associated cover strip 51, 52 and responsively control speed of the first and second motors 160, 170 to increase or decrease the speed of rotation, length of time of rotation or both of the flanged spools 141, 151 carrying the cover strips 51,52. This constant tension accommodates any difference in length of the cover strips after their separation from each other to sequentially and uniformly feed the bandage supply 50 through dispenser apparatus 100, notwithstanding any difference in length of the cover strips 51, 52. This same function that as stated is accomplished with two tension sensors 180, 190 may be accomplished, if not so well, with one tension sensor in one waste course to maintain constant predetermined tension in that waste path, and such modification is within the spirit and scope of my invention.

Movement of the first and second cover strips 51, 52 in the manner aforesaid causes the cover strips to separate from one another at the cover strip separator device 130, whereupon the given bandage 53a is caused to be exposed and to pass through the slot 119 and out from the casement 110. In this manner, the given bandage 53a is dispersed to the operator of the dispenser apparatus 100 for use.

When the bulk bandage supply 50 is depleted from the bandage support device 120, the top panel 117 is removed to gain access to the internal components of the casement 110. The empty reel 121 is removed from the axle 122, and the flanged spools 141, 151, which now contain respective coiled rolls of cover strips 51, 52, are removed from the casement 110. Another reel 121 containing a full bandage supply 50 is replaced on the axle 122. Empty flanged spools 141, 151 are replaced on respective axles 142, 152. The top panel 117 is then replaced and the dispenser apparatus 100 is again ready to dispense bandages in the manner as specified hereinbefore.

While the invention set forth herein has been described in language more or less specific as to structural and methodical features, it is to be understood that the invention is not intended to be limited to the specific features shown and described, since the means herein disclosed comprise only preferred forms of putting the invention into effect. The invention is, therefore, claimed in any of its forms or modifications within the proper scope of the appended claims appropriately interpreted in accordance with the doctrine of equivalents.

What is claimed is:

1. An apparatus for dispersing a bandage supply having strip bandages carried between a first elongate cover strip and a second elongate cover strip, the apparatus comprising in combination:
    a casement;
    a bandage support device supported on the casement to disperse the bandage supply responsive to predetermined tensive force;
    a cover strip separator device at which the first cover strip and the second cover strip are separated from a given strip bandage;
    a first cover strip take-up device supported on the casement and configured to accumulate the first cover strip;
    a second cover strip take-up device supported on the casement and configured to accumulate the second cover strip;
    a first motor in power-transmitting engagement with the first cover strip takeup device; and
    a second motor in power-transmitting engagement with the second cover strip take-up device, wherein:
    a main bandage path is defined from the bandage support device to the cover strip separator device;
    a first waste path is defined from the cover strip separator device to the first cover strip take-up device;
    a second waste path is defined from the cover strip separator device to the second cover strip take-up device; and
    at least one waste path having an associated tension sensor carried by the casement to sense tension in the covering strip in the at least one waste path and responsively control the motor in power transmitting engagement with the take-up device carrying the cover strip in the at least one waste path to regulate tension in the said cover strip to a predetermined valve.

2. The apparatus of claim 1 further comprising a manually operable control switch supported by the casement and in controllable linkage with the first and second motors to start and stop said motors.

3. The apparatus of claim 1 wherein the bandage support device is substantially in the form of a reel that is rotatable relative to the casement, and wherein a bandages supply along with the first cover strip and the second cover strip is uncoiled from the bandage support device during dispersion of a given bandage.

4. The apparatus of claim 3 wherein the first cover strip take-up device and the second cover strip take-up device are each substantially in the form of a reel that is rotatable with respect to the casement, and wherein the first cover strip is wound about the first cover strip take up device and the second cover strip is wound about the second cover strip take-up device during dispersion of a given bandage.

5. The apparatus of claim 1 wherein the strip bandages are carried between the first cover strip and the second cover strip in an end-to-end orientation.

* * * * *